United States Patent
Fukuzawa et al.

(10) Patent No.: US 9,255,276 B2
(45) Date of Patent: Feb. 9, 2016

(54) METHOD OF TRANSFERRING GENE INTO ALGAL CELL INVOLVING UTILIZING MULTIPLE SQUARE-WAVE PULSES IN THREE STEPS

(71) Applicants: Kyoto University, Kyoto (JP); Nepa Gene Co., Ltd., Chiba (JP)

(72) Inventors: Hideya Fukuzawa, Kyoto (JP); Takashi Yamano, Kyoto (JP); Kentaro Ifuku, Kyoto (JP); Yasuhiko Hayakawa, Chiba (JP)

(73) Assignees: Kyoto University, Kyoto (JP); Nepa Gene Co., Ltd., Chiba (JP)

( * ) Notice: Subject to any disclaimer, the term of this patent is extended or adjusted under 35 U.S.C. 154(b) by 56 days.

(21) Appl. No.: 14/176,703

(22) Filed: Feb. 10, 2014

(65) Prior Publication Data
US 2015/0011008 A1    Jan. 8, 2015

(30) Foreign Application Priority Data
Jul. 2, 2013 (JP) .................................. 2013-138581

(51) Int. Cl.
  *C12N 15/87* (2006.01)
  *C12N 15/74* (2006.01)
  *C12N 15/82* (2006.01)
  *A61N 1/04* (2006.01)

(52) U.S. Cl.
  CPC ............ *C12N 15/8206* (2013.01); *A61N 1/0412* (2013.01)

(58) Field of Classification Search
  CPC .......................... C12N 15/8206; A61N 1/0412
  See application file for complete search history.

(56) References Cited

PUBLICATIONS

Holo et al., High-Frequency Transformation, by Electroporation, of *Lactococcus lactis* subsp. cremoris Grown with Glycine in Osmotically Stabilized Media, Applied and Environmental Microbiology, Dec. 1989, p. 3119-3123.*
Brown et al., Introduction of Exogenous DNA into *Chlamydomonas reinhardtii* by Electroporation, Molecular and Cellular Biology, Apr. 1991, p. 2328-2332.*
Jeon et al., Highly efficient molecular delivery into *Chlamydomonas reinhardtii* by electroporation, Korean J. Chem. Eng., 30(8), 1626-1630 (2013).*
Bureau et al., Importance of association between permeabilization and electrophoretic forces for intramuscular DNA electrotransfer, Biochimica et Biophysica Acta 1474 (2000) 353^ 359.*
Karen L. Kindle, "High-frequency nuclear transformation of *Chlamydomonas reinhardtii*" Proc. Natil. Acad. Sci. USA, vol. 87, Feb. 1990, pp. 1228-1232.

(Continued)

*Primary Examiner* — Reza Ghafoorian
(74) *Attorney, Agent, or Firm* — Oblon, McClelland, Maier & Neustadt, L.L.P.

(57) ABSTRACT

A method of transferring an exogenous gene into a eukaryotic algal cell, the method including performing electroporation using multiple square-wave pulses to the solution containing a cell of a green alga with cell-wall, and a nucleic acid molecule by the following three steps: applying a square-wave electric pulse (first electric pulse) with a high voltage for a short period of time under the condition that its total electric energy falls within a predetermined range; then applying a square-wave electric pulse (second electric pulse) with a low voltage for a long period of time two or more times; and then applying a square-wave electric pulse (third electric pulse) that is opposite in polarity to the second electric pulse, with a low voltage for a long period of time, two or more times.

12 Claims, 5 Drawing Sheets

(56) References Cited

PUBLICATIONS

Kosuke Shimogawara, et al., "High-Efficiency Transformation of *Chlamydomonas reinhardtii* by Electroporation" Genetics, vol. 148, Apr. 1998, pp. 1821-1828.

John E. Boynton, et al., "Chloroplast Transformation in *Chlamydomonas* with High Velocity Microprojectiles" Science, vol. 240, 1998, pp. 1534-1538.

Alan. D. Blowers, et al., "Studies on *Chlamydomonas* Chloroplast Transformation: Foreign DNA Can Be Stably Maintained in the Chromosome" The Plant Cell, vol. 1, Jan. 1989, pp. 123-132.

S. I. Sukharev, et al., "Electroporation and electrophoretic DNA transfer into cells; The effect of DNA interaction with electropores" Biophysical Journal, vol. 63, Nov. 1992, pp. 1320-1327.

\* cited by examiner

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: PCR primer for amplifying aph7

<400> SEQUENCE: 1 gcacccagg ctttacactt tatgcttcc                                29

<210> SEQ ID NO 2
<211> LENGTH: 24
<212> TYPE: DNA
<213> ORGANISM: Artificial Sequence
<220> FEATURE:
<223> OTHER INFORMATION: PCR primer for amplifying aph7

<400> SEQUENCE: 2
ccattcaggc tgcgcaactg ttgg                                    24

METHOD OF TRANSFERRING GENE INTO ALGAL CELL INVOLVING UTILIZING MULTIPLE SQUARE-WAVE PULSES IN THREE STEPS

BACKGROUND OF THE INVENTION

1. Field of the Invention

The present invention relates to a technology for efficiently transferring a gene into a eukaryotic algal cell with cell-wall, by performing electroporation through application of multiple square-wave pulses in three steps with total electric energy of a first electric pulse adjusted within a predetermined range.

2. Description of the Related Art

Technical problem in gene transfer into eukaryotic algae

In recent years, novel and useful species of eukaryotic algae have been discovered one after another, and utilization of microalgae that produce oils and fats through photosynthesis is expected to be a key to next-generation biofuel production. Accordingly, in order to produce strains of those algae having useful traits, there has been a demand for development of gene transfer and transformation technologies.

However, cells of the eukaryotic algae have thick cell walls for protecting the cells as with general plant cells, and hence significant technical problems exist in performing gene transfer and transformation.

As a current transformation technology for eukaryotic algal cells, specifically, there may be given (1) a 'glass bead method,' which involves allowing algal cells, DNA to be transferred, and glass beads to coexist in a solution, and agitating the solution vigorously for a certain period of time, thereby causing damage to the cells to transfer the DNA into the cells (see Kindle, K.: High-frequency nuclear transformation of *Chlamydomonas reinhardtii*. Proc. Natl. Acad. Sci. USA, 87, p 1228-1232 (1990)). In addition, (2) an 'electroporation method' has also been performed, which involves allowing algal cells and DNA to be transferred to coexist in a solution, and discharging a current charged in a capacitor, thereby causing damage to the cells to transfer the DNA into the cells (see Shimogawara, K., Fujiwara, S., Grossman, A., and Usuda, H.: High-efficiency transformation of *Chlamydomonas reinhardtii* by electroporation. Genetics, 148, p 1821-1828 (1998)).

However, in each of the glass bead method and the electroporation method, it is necessary to perform the gene transfer under a state in which the target algal cells have been converted into "protoplasts," i.e., the cell walls have been removed from the cells. Accordingly, when any of those methods is performed, it is necessary to establish systems for the conversion into protoplasts and their regeneration depending on the species of the target alga. (It should be noted that, when the protoplasts are not prepared, it is necessary to produce a cell wall-less special mutant strain.)

Therefore, it is recognized to be difficult in reality to use any of those methods for most species of algae other than certain algae (e.g., *Chlamydomonas reinhardtii*). In addition, the following problem has been pointed out. That is, when any of those methods is performed for *Chlamydomonas reinhardtii* or the like, the conversion into protoplasts and their regeneration are time-consuming processes, and hence reproducibility is low depending on experimenters.

In addition, as a method that allows the preparation of protoplasts to be omitted, there is given (3) a method involving using a 'gene gun (particle gun).' The method is a method involving preparing gold particles or tungsten particles coated with DNA to be transferred, and shooting the particles into cells with gunpowder or a nitrogen gun to transfer the DNA into the cells (see Boynton, J., Gillham, N., Harris, E., Hosler, J., Johnson, A., Jones, A., Randolph-Anderson, B., Robertson, D., Klein, T., Shark, K., and Sanford, J.: Chloroplast transformation in *Chlamydomonas* with high velocity microprojectiles. Science, 240, p 1534-1538 (1998), and Blowers, A., Bogorad, L., Shark, K., and Sanford, J.: Studies on *Chlamydomonas* chloroplast transformation: foreign DNA can be stably maintained in the chromosome. Plant Cell, 1, p 123-132 (1989)).

However, the method needs an expensive and special device and costly consumables, and requires a long period of time for sample preparation. Hence, the method is recognized to be difficult to utilize with general laboratory-level equipment. There is also a problem in that the method is not suitable for performing high-throughput or large-scale treatment. Further, the following problem has also been pointed out. That is, sufficient transformation efficiency cannot be expected because of its low gene transfer frequency.

Necessity of Gene Transfer Technology for Eukaryotic Algae

As described above, technical problems exist in transferring an exogenous gene into eukaryotic algal cells, and gene transfer into species of algae other than certain species such as *Chlamydomonas reinhardtii* is substantially difficult in the present situation. Accordingly, there has been desired development of a highly general-purpose gene transfer method that is applicable to any species of algae. In particular, there is a demand for development of a technology that is readily applicable to various useful algae such as green algae and diatoms.

In addition, also in the case of performing gene transfer into *Chlamydomonas reinhardtii* or the like, it is necessary to prepare gametolysin, which is a cell wall lytic enzyme, and hence there has been desired development of a method that enables efficient gene transfer within a shorter period of time.

SUMMARY OF THE INVENTION

An object of the present invention is to provide a technology that solves the above-mentioned problems, and is directly applicable to eukaryotic algal cells with cell-wall, the technology enabling gene transfer and transformation to be performed with high efficiency and good reproducibility irrespective of species of algae.

The inventors of the present invention have made extensive studies in order to attain the object, and as a result, have found that gene transfer and transformation can be performed for eukaryotic algal cells with cell-wall with high efficiency in a stable manner by performing electroporation using multiple square-wave pulses by the following three steps: applying a square-wave electric pulse (first electric pulse) with a high voltage for a short period of time under the condition that its total electric energy falls within a predetermined range; then applying a square-wave electric pulse (second electric pulse) with a low voltage for a long period of time two or more times; and then applying a square-wave electric pulse (third electric pulse) that is opposite in polarity to the second electric pulse, with a low voltage for a long period of time, two or more times.

In particular, the inventors of the present invention have found that a particularly important technical feature is to satisfy "the condition such that the total electric energy of the first electric pulse falls within a predetermined range" among those electric conditions.

The inventors of the present invention have also found that the electroporation method that satisfies the electric conditions is a technology that is widely applicable to green algae and diatoms irrespective of certain species of algae.

It should be noted that, in this context, in an electroporation method that is generally performed for eukaryotic algal cells as a related art, there has been often used a method involving applying an electric pulse once from an output device that adopts "decay wave system (exponential system)" to suspended cells (see, for example, Shimogawara, K., Fujiwara, S., Grossman, A., and Usuda, H.: High-efficiency transformation of *Chlamydomonas reinhardtii* by electroporation. Genetics, 148, p 1821-1828 (1998)). In addition, as a technology for mammalian cells, there has been disclosed a method involving applying two different types of electric pulses to perform efficient gene transfer into mammalian cells (see Sukharev 5.1., Klenchin V. A., Serov S. M., Chemomordik L. V., and Chizmadzhev Yu. A.: Electroporation and electrophoretic DNA transfer into cells. Biophys. J., 63, p 1320-1327 (1992)).

However, when electroporation is performed for an "alga with cell-wall" by any of the methods described in those documents, gene transfer efficiency shows a remarkably low value. Accordingly, when electroporation based on any of those technologies is applied, it is necessary to convert target algal cells into protoplasts before applying electric pulses.

The present invention has been made based on those findings.

That is, the invention according to a first aspect relates to a method of transferring an exogenous gene into a eukaryotic algal cell, the method including performing electroporation using multiple square-wave pulses by the following three steps:

applying a square-wave electric pulse that satisfies a condition as defined in the following item (A) to a solution one time, two times or more so that the square-wave electric pulse has a total electric energy of 1.3 to 4.9 J/100 µL, the solution containing a cell of a green alga with cell-wall, and a nucleic acid molecule;

applying a square-wave electric pulse that satisfies conditions as defined in the following items (B1) and (B2) to the solution at least two times; and applying a square-wave electric pulse that satisfies conditions as defined in the following items (C1) to (C3) to the solution at least two times:

(A) a square-wave electric pulse having a voltage per pulse of 750 V/cm or more;

(B1) a square-wave electric pulse having a voltage per pulse of 150 V/cm or less;

(B2) a square-wave electric pulse having an electric energy per pulse of 0.02 to 0.6 J/100 µL;

(C1) a square-wave electric pulse opposite in polarity to the electric pulse that satisfies the conditions as defined in the items (B1) and (B2);

(C2) a square-wave electric pulse having a voltage per pulse of 150 V/cm or less; and (C3) a square-wave electric pulse having an electric energy per pulse of 0.02 to 0.6 J/100 µL.

In addition, the invention according to a second aspect relates to a method of transferring an exogenous gene into a eukaryotic algal cell, the method including performing electroporation using multiple square-wave pulses by the following three steps:

applying a square-wave electric pulse that satisfies a condition as defined in the following item (A) to a solution one time, two times or more so that the square-wave electric pulse has a total electric energy of 3.3 to 14.3 J/100 µL, the solution containing a cell of a diatom with cell-wall, and a nucleic acid molecule;

applying a square-wave electric pulse that satisfies conditions as defined in the following items (B1) and (B2) to the solution at least two times; and applying a square-wave electric pulse that satisfies conditions as defined in the following items (C1) to (C3) to the solution at least two times:

(A) a square-wave electric pulse having a voltage per pulse of 750 V/cm or more;

(B1) a square-wave electric pulse having a voltage per pulse of 150 V/cm or less;

(B2) a square-wave electric pulse having an electric energy per pulse of 0.02 to 0.6 J/100 µL;

(C1) a square-wave electric pulse opposite in polarity to the electric pulse that satisfies the conditions as defined in the items (B1) and (B2);

(C2) a square-wave electric pulse having a voltage per pulse of 150 V/cm or less; and (C3) a square-wave electric pulse having an electric energy per pulse of 0.02 to 0.6 J/100 µL.

In addition, the invention according to a third aspect relates to a method according to the first or second aspect, in which the green alga or the diatom includes a unicellular microalga.

In addition, the invention according to a forth aspect relates to a method according to any one of the first to third aspects, in which the applying of the square-wave electric pulse that satisfies the condition as defined in the following item (A) is performed at least two times:

(A) a square-wave electric pulse having a voltage per pulse of 750 V/cm or more.

In addition, the invention according to a fifth aspect relates to a method according to any one of the first to fourth aspects, in which:

the applying of the square-wave electric pulse that satisfies the conditions as defined in the following items (B1) and (B2) is performed at least five times; and the applying of the square-wave electric pulse that satisfies the conditions as defined in the following items (C1) to (C3) is performed at least five times:

(B1) a square-wave electric pulse having a voltage per pulse of 150 V/cm or less;

(B2) a square-wave electric pulse having an electric energy per pulse of 0.02 to 0.6 J/100 µL;

(C1) a square-wave electric pulse opposite in polarity to the electric pulse that satisfies the conditions as defined in the items (B1) and (B2);

(C2) a square-wave electric pulse having a voltage per pulse of 150 V/cm or less; and (C3) a square-wave electric pulse having an electric energy per pulse of 0.02 to 0.6 J/100 µL.

In addition, the invention according to a sixth aspect relates to a method according to any one of the first to fifth aspects, in which the electroporation is performed using a cuvette electrode with a gap of 2 mm or more.

In addition, the invention according to a seventh aspect relates to a method according to any one of the first to sixth aspects, in which the cell is suspended in the solution.

In addition, the invention according to an eighth aspect relates to a method of transforming a eukaryotic algal cell, the method including performing gene transfer by the method according to any one of the first to seventh aspects.

DETAILED DESCRIPTION OF THE PREFERRED EMBODIMENTS

Figure 1:
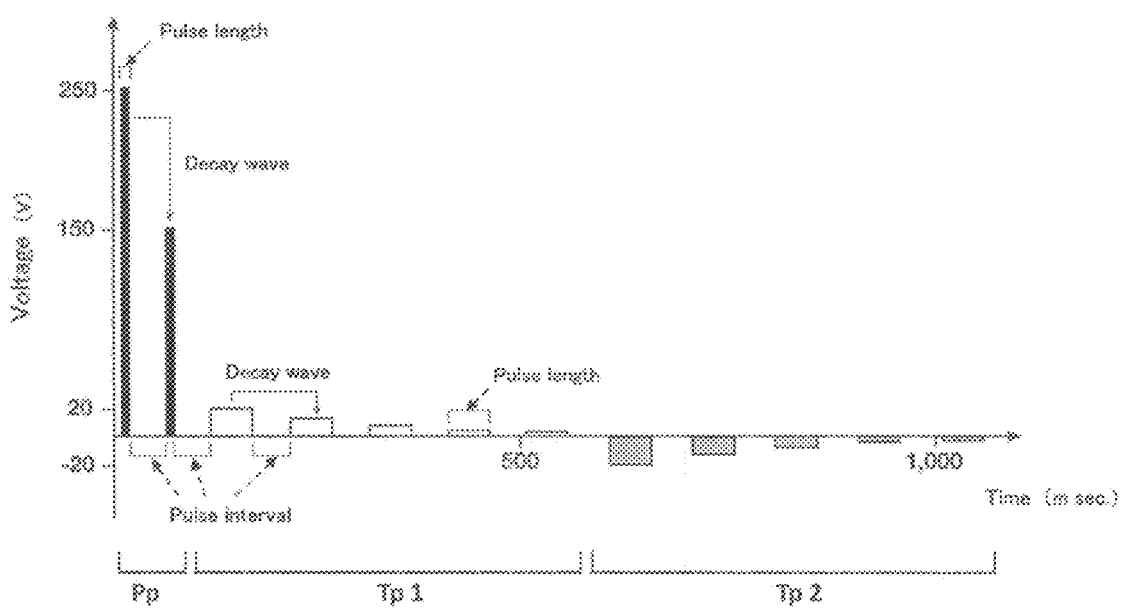
FIG. 1 is a diagram illustrating the concept of an electroporation method involving performing electroporation using multiple square-wave pulses in three steps according to the present invention, in which the vertical axis represents voltage (V) and the horizontal axis represents time (msec), and in which "Pp" represents a poring pulse and "Tp" represents a transfer pulse.

Hereinafter, embodiments of the present invention are described in detail.

The present invention relates to a technology for efficiently transferring an exogenous gene into eukaryotic algal cells with cell-wall by performing electroporation through the application of multiple square-wave pulses in three steps with the total electric energy of a first electric pulse adjusted within a predetermined range.

(Eukaryotic Algal Cell)

An electroporation method of the present invention is a technology that uses "eukaryotic algal cells with cell-wall" as gene transfer targets.

In this context, the term 'eukaryotic algae' refers to eukaryotic organisms that perform photosynthesis, but the technology of the present invention specifically uses algae classified as green algae or diatoms as targets. Those cells have common properties in that the cells have thick cell walls outside cell membranes.

The reason why electroporation based on a conventional method is not directly applicable to those cells lies in that the thick cell walls inhibit gene transfer. That is, when the general electroporation method that has been applied to bacteria or animal cells (e.g., mammals and insects) is merely performed, gene transfer and transformation cannot be performed for eukaryotic algal cells at a level sufficient for practical use.

It is recognized that the technology of the present invention is applicable to any species of eukaryotic alga belonging to the green algae or the diatoms as long as the kind and thickness of its cell wall are those of the cell wall of an alga that normally exists in nature.

In this context, the term 'green algae' refers to green algae having chloroplasts containing chlorophylls a and b (green algae in a broad sense). The green algae may also be defined as a group consisting of Viridiplantae excluding land plants (bryophytes, pteridophytes, gymnosperms, and angiosperms).

The green algae include an extremely huge variety of species of algae ranging from unicellular to multicellular ones. Specific examples thereof may include algae belonging to the class Chlorophyceae (green algae in a narrow sense: e.g., *Chlamydomonas* sp., *Volvox* sp., *Gonium* sp., *Botryococcus* sp., *Pediastrum* sp., and *Scenedesmus* sp.), the class Ulvophyceae (e.g., *Enteromorpha* sp., *Ulva pertusa* Kjellman, *Codium* sp., and *Actabularia* sp.), and the class Charophyceae (e.g., *Chara* sp., *Coleochaete* sp., *Closterium* sp., *Cosmarium* sp., *Spirogyra* sp., and *Chaetosphaeridium* sp.).

In addition, many useful algae such as oil-producing green algae have been being discovered, and hence the green algae are a group to which the gene transfer technology of the present invention is expected to be applied. In addition, genomic and genetic analyses of *Chlamydomonas reinhardtii* have been extremely highly advanced and many gene mutants thereof have been accumulated as well.

Many species of green algae are surrounded by thick cell walls containing polysaccharides including cellulose as main components, but the gene transfer technology of the present invention is applicable to any species thereof as long as the kind and thickness of its cell wall are those of a cell wall found in a wild type.

It should be noted that the technology of the present invention is suitably applicable to cells of green algae belonging to preferably the order Volvocales (order Volvocida), to which *Chlamydomonas reinhardtii* belongs, more preferably the family Chlamydomonadaceae, still more preferably the genus *Chlamydomonas*. This is because it is recognized that the cell walls of those algal cells have particularly similar properties to those of the cell wall of *Chlamydomonas reinhardtii* among the green algae.

It should be noted that the group of the so-called 'plants,' i.e., land plants (bryophytes, pteridophytes, gymnosperms, and angiosperms) originate from relatives of *Chara* algae, part of green algae, which appeared on land and underwent adaptive radiation on land about 450,000,000 to 500,000,000 years ago. However, the plants are species that have highly differentiated multicellularity, and are a group that have undergone, for example, secondary thickening or lignification of cell walls for adaptation to dry conditions in association with their appearance on land. Accordingly, it is unknown whether or not the technology of the present invention is applicable thereto in principle.

In this context, the term 'diatoms' refers to a group of algae that constitute the Chrysophyta (Heterokontophyta) and are brown in color owing to the properties of chloroplasts. All diatoms are unicellular species, and account for many of freshwater and sea-water plankton. In addition, the diatoms cause red tides. Specific examples thereof may include diatoms of the order Pennales (e.g., *Phaeodactylum* sp., *Cylindrotheca* sp., and *Navicula* sp.) and diatoms of the order Centrales (such as *Cyclotella* sp., *Thalassiosira* sp., and *Chaetoceros* sp.). Among the diatoms exist species that are commercially important because of having siliceous frustules and producing useful lipids. In addition, *Phaeodactylum tricornutum*, which is unicellular, is a species that has been analyzed in detail as a representative species of diatom cells.

Many species of diatoms are surrounded by siliceous thick cell walls (frustules), but it is recognized that the gene transfer technology of the present invention is applicable to any species thereof as long as the kind and thickness of its cell wall are those of a cell wall (frustule) found in a wild type.

It should be noted that the technology of the present invention is suitably applicable to cells of diatoms belonging to preferably the order Pennales (order Naviculales), to which *Phaeodactylum tricornutum* belongs, more preferably the family Phaeodactylaceae, still more preferably the genus *Phaeodactylum*. This is because it is recognized that the cell walls of those algal cells have particularly similar properties to those of the cell wall of *Phaeodactylum tricornutum* among the diatoms.

The technology of the present invention is particularly effective for 'unicellular microalgae.' This is because electroporation treatment can be directly performed for algal cells prepared through culture, harvest, and the like without performing any special cell treatment. Another reason is that culture can be directly performed after gene transfer without any need for regeneration treatment or the like.

It should be noted that, in order to apply the gene transfer technology of the present invention to 'multicellular algae,' it is necessary to treat a plant body so as to have a size that can be accommodated in a cuvette. For example, from the viewpoints of gene transfer efficiency and transformation efficiency, it is suitable to perform electroporation treatment under a state in which the multicellular algae have been separated into single cells or aggregates of several cells through treatment with a cell wall lytic enzyme or the like. In addition, from the viewpoint of facilitating tissue regeneration after gene transfer, it is desirable to perform electroporation treatment under a state in which the multicellular algae have been subjected to shredding, tissue detachment, or the like to prepare tissue fragments.

(Electroporation Treatment)

It is essential for the technology of the present invention to perform treatment of applying, to a solution containing the algal cells and a nucleic acid molecule, multiple square-wave pulses in three steps that satisfy predetermined electric pulse conditions (electroporation treatment).

Electroporation Buffer

The electroporation treatment is performed by charging an electrode solution into an electrode container with the solution containing the target algal cells and the nucleic acid molecule to be transferred.

In this case, as the solution (electroporation buffer), a liquid medium to be used for culturing freshwater algae may be used as it is or after dilution with water. That is, it is not necessary to purchase or prepare any special electroporation buffer. In addition, in the case of sea-water algae, a medium having no or significantly reduced salt content may be used. In this regard, however, the solution desirably has an osmotic pressure adjusted so as to be isotonic with the cytoplasm through the addition of a saccharide (e.g., sucrose, mannitol, or sorbitol). This is because damage to the cells at the time of the electroporation can be reduced.

In addition, it is suitable to use, as the solution, a medium containing no antibiotic (antibiotic-free medium). This is because, when an antibiotic is present in the solution, the antibiotic is incorporated into the cells through the electroporation treatment, resulting in a decrease in the viability of the cells. It should be noted that the incorporation of an antibiotic is permitted as long as its concentration is low (e.g., 1% or less, preferably 0.5% or less).

Nucleic Acid Molecule

In this context, the term 'nucleic acid molecule' widely refers to exogenous nucleic acid molecules (e.g., DNA, RNA, and RNP) to serve as objects to be transferred, and DNA is envisaged as a main object to be transferred. The DNA preferably has a linearized shape (e.g., a PCR product or a restriction enzyme-treated product), but may be in a circular state like a plasmid or the like. In addition, an oligonucleotide, siRNA, antisense RNA, or a viral vector may also be transferred.

In addition, as sequence information, there may be given cDNA having a gene sequence and a sequence of genomic DNA. The sequence information includes not only the full-length sequence of a gene, but also a partial sequence, a regulatory region, a spacer region, a mutant sequence, a construct sequence, and the like of a gene.

It is suitable that the concentration of the nucleic acid to be incorporated into the solution (electroporation buffer) be 0.5 µg/mL or more, preferably 1 µg/mL or more, more preferably µg/mL or more, still more preferably 2.5 µg/mL or more, particularly preferably 3 µg/mL or more, even more preferably 4 µg/mL or more, still even more preferably 4.5 µg/mL or more, yet still even more preferably 5 µg/mL or more. The case where the nucleic acid concentration is excessively low is not preferred because gene transfer efficiency lowers.

It is suitable that the upper limit of the nucleic acid concentration be 200 µg/mL or less, preferably 150 µg/mL or less, more preferably 125 µg/mL or less, still more preferably 100 µg/mL or less, particularly preferably 75 µg/mL or less, even more preferably 50 µg/mL or less, still even more preferably 40 µg/mL or less, yet still even more preferably 30 µg/mL or less, particularly even more preferably 25 µg/mL or less. The case where the nucleic acid concentration is excessively high is not preferred because the viability of the cells decreases, resulting in a decrease in transformation efficiency.

In consideration of the foregoing, when the nucleic acid concentration is 1 to 100 µg/mL, preferably 2.5 to 50 µg/mL, more preferably 5 to 25 µg/mL, gene transfer and transformation can be performed with particularly high efficiency.

Cell Concentration

The concentration of the cells to be incorporated into the solution (electroporation buffer) is desirably adjusted within the range of $10^6$ to $10^9$ cells/mL, preferably $5\times10^6$ to $5\times10^8$ cells/mL, more preferably $5\times10^7$ to $2.5\times10^8$ cells/mL, still more preferably $2.5\times10^7$ to $10^8$ cells/mL.

It should be noted that, in the preparation of the solution containing the algal cells and the nucleic acid, it is desirable to perform an operation of agitation, for example, by pipetting or with a vortex mixer for several seconds to achieve a state in which the algal cells and the nucleic acid are thoroughly mixed in the solution. A state in which the cells are suspended at the time of the electroporation treatment is most suitable. It should be noted that so excessive performance of the operation of agitation or the like that the solution is brought into a foamed state is not preferred.

Device

In order to perform the electroporation treatment, any device may be used as long as the device can output multiple square-wave pulses in three steps that satisfy predetermined electric pulse conditions to be described later.

For example, an electric pulse-outputting device "NEPA21 (trademark)" from Nepa Gene Co., Ltd. may be suitably used. This device has a function of measuring an electrical impedance value and a current value for each treatment, and hence electric conditions can be set in detail. The device also has a function of switching electrical polarity for each electric pulse when applying multiple electric pulses.

It should be noted that, although the electroporation may be performed by devising a way to use a conventional square pulse system electric pulse-outputting device, this is not suitable because electric energy at the time of the electroporation cannot be determined with the function of the device.

The electroporation treatment is performed with a cuvette electrode holder connected to the electric pulse-outputting device and an electrode container (cuvette electrode) for receiving the cell/nucleic acid mixed solution. An electric pulse output from the electric pulse-outputting device is output through the cuvette electrode-holding container to the cuvette electrode inserted in the electrode container, and is conducted to the cells in the electrode container.

As the cuvette electrode, any one may be used as long as it has a capacity for general use. For example, there may be used a cuvette electrode with a gap of 1 mm (capacity: 20 to 70 µm), a gap of 2 mm (capacity: 40 to 400 µm), or a gap of 4 mm (capacity: 80 to 800 µm). Suitably, through the use of a 2-mm gap cuvette or a cuvette having a larger capacity (2-mm gap cuvette or 4-mm gap cuvette), results of both gene transfer efficiency and transformation efficiency can be stabilized.

The electroporation treatment may be performed at room temperature (e.g., about 10 to 35° C.). It should be noted that it is recommended to avoid cooling with ice in order to prevent a water droplet from adhering to a metal part of the electrode container.

(Electric Pulse Conditions)

The method of the present invention includes performing electroporation using multiple square-wave pulses by the following three steps: applying a square-wave electric pulse (first electric pulse) with a high voltage for a short period of time under predetermined conditions to the solution containing the algal cells and the nucleic acid molecule; then applying a square-wave electric pulse (second electric pulse) with a low voltage for a long period of time to the solution two or more times; and then applying a square-wave electric pulse (third electric pulse) that is opposite in polarity to the second electric pulse, with a low voltage for a long period of time, to the solution two or more times (see, for example, FIG. 1).

It is required that both the 'voltage' and 'electric energy' of each of the first to third electric pulses in the present invention fall within certain ranges to be described later.

The voltage in this context is a value representing a voltage V to be applied per unit cm of the width between electrodes in the electrode container (specifically, the width of the cuvette electrode). For example, in order to apply a voltage of 300 V/cm, the voltage to be applied is 30 V for a 1-mm gap cuvette, 60 V for a 2-mm gap cuvette, and 120 V for a 4-mm gap cuvette.

In addition, the electric energy (W) in this context is a value representing electric energy (energy amount) to be applied per 100 µL of the solution. For example, when a voltage (V) of 150 V is applied to 100 µL of a solution having a impedance value of 50Ω for a time (T) of 5 msec in terms of pulse length, a current (I) of 3 A is generated. In this case, the electric energy (W=VIT) to be applied per 100 µL of the solution is 2.25 J.

In addition, it is required to apply 'square-wave' electric pulses as the electric pulses of the present invention. With 'decay wave' electric pulses, the gene transfer efficiency of the present invention cannot be attained.

First Electric Pulse: Poring Pulse (Pp)

The electroporation treatment of the present invention is the technology for which it is essential to apply the square-wave electric pulse (first electric pulse: poring pulse) with a high voltage for a short period of time under predetermined conditions. Through the application of the first electric pulse, small pores can be formed in the cell walls of the algal cells with a small degree of damage.

It should be noted that, in an electroporation method for bacteria or animal cells (conventional method), although there is a finding that increasing the voltage of the first electric pulse allows a nucleic acid molecule (e.g., DNA or RNA) to be transferred into cells, gene transfer at a practical level cannot be attained for algal cells (plant cells) by merely increasing the voltage. This is because, when the damage to the cell walls is severe, the viability of the cells subjected to the electroporation treatment remarkably decreases.

In the first electric pulse, it is necessary to apply a voltage of at least 750 V/cm or more (150 V or more in the case of a 2-mm gap cuvette). It is desirable to apply a voltage of preferably 800 V/cm or more, more preferably 850 V/cm or more, still more preferably 900 V/cm or more, particularly preferably 950 V/cm or more, even more preferably 1,000 V/cm or more. This is because, when the voltage is excessively low, small pores cannot be formed in the cell walls.

It should be noted that the first electric pulse may be applied without any particular limitation on the upper limit of its voltage value as long as a condition for the total electric energy to be described later is satisfied. This is because the degree of damage to the cell walls depends not on the value of the voltage but on the value of the 'total electric energy (energy amount).'

It is essential that the 'total electric energy' of the first electric pulse fall within a predetermined range. In this context, the total electric energy is a value showing the total value of the electric energy of electric pulses each having the above-mentioned voltage value or higher. For example, when an electric pulse of 750 V/cm or more is applied two times, the total value of the electric energy of the two times of electric pulses is defined as the value of the total electric energy.

When cells of a green alga are used as targets, it is essential that the total electric energy be 1.3 J/100 µL or more. When the total electric energy is excessively low, sufficient gene transfer efficiency cannot be attained. The lower limit of the total electric energy may be, for example, preferably 1.7 J/100 µL or more, more preferably 1.9 J/100 µL or more, still more preferably 2.1 J/100 µL or more, particularly preferably 2.4 J/100 µL or more, even more preferably 2.7 J/100 µL or more.

In addition, it is essential that the upper limit of the total electric energy be 4.9 J/100 µL or less. The case where the total electric energy is excessively high is not preferred because damage to the cell walls or the cell membranes increases, resulting in a decrease in viability. The upper limit of the total electric energy may be, for example, preferably 4.8 J/100 µL or less, more preferably 4.6 J/100 µL or less, still more preferably 4.3 J/100 µL or less, particularly preferably 3.8 J/100 µL or less, even more preferably 3.3 J/100 µL or less.

In consideration of the foregoing in a comprehensive manner, it is suitable that the total electric energy be 1.3 to 4.9 J/100 μL, preferably 1.7 to 4.8 J/100 μL, more preferably 1.9 to 4.6 J/100 μL, still more preferably 2.1 to 4.3 J/100 μL, particularly preferably 2.4 to 3.8 J/100 μL, even more preferably 2.7 to 3.3 J/100 μL, most preferably around 3 J/100 μL. The condition for the total electric energy corresponds to a condition for suppressing damage to the cell walls and the cell membranes while forming, in the cell walls, small pores suitable for the incorporation of a nucleic acid.

When cells of a diatom are used as targets, it is essential that the total electric energy be 3.3 J/100 μL or more. When the total electric energy is excessively low, sufficient gene transfer efficiency cannot be attained. The lower limit of the total electric energy may be, for example, preferably 4.8 J/100 μL or more, more preferably 6.5 J/100 μL or more, still more preferably 7.5 J/100 μL or more.

In addition, it is essential that the upper limit of the total electric energy be 14.3 J/100 μL or less. The case where the total electric energy is excessively high is not preferred because damage to the cell walls and the cell membranes increases, resulting in a decrease in viability. The upper limit of the total electric energy may be, for example, preferably 12.9 J/100 μL or less, more preferably 11.3/100 μL or less, still more preferably 10.2 J/100 μl or less.

In consideration of the foregoing in a comprehensive manner, it is suitable that the total electric energy be 3.3 to 14.3 J/100 μL, preferably 4.8 to 12.9 J/100 μL, more preferably 6.5 to 11.3 J/100 μL, still more preferably 7.5 to 10.2 J/100 μL, most preferably around 8.9 J/100 μL. The condition for the total electric energy corresponds to a condition for suppressing damage to the cell walls and the cell membranes while forming, into the cell walls, small pores suitable for the incorporation of a nucleic acid.

It should be noted that the first electric pulse may be applied without any particular limitation on the number of times of its application as long as the total electric energy falls within the above-mentioned range. For example, the electric pulse may be applied at one time within the above-mentioned range of the electric energy, or the electric pulse may be applied two or more times by dividing the electric energy. Specifically, the number of the times may be, for example, 2 to 10. When the electric pulses are applied separately for a plurality of times, an effect of slightly reducing the degree of damage to the cell walls is expected.

It should be noted that an interval between pulses in the case of the plurality of times of the application of the pulse may be, for example, 200 msec or less, preferably 100 msec or less, more preferably 75 msec or less, still more preferably 50 msec or less.

In addition, in the present invention, the pulse length and decay rate of the first electric pulse are factors for determining the electric energy, but do not show direct correlations with gene transfer efficiency and transformation efficiency.

Second Electric Pulse: Transfer Pulse 1 (Tp1)

The electroporation treatment of the present invention is the technology for which it is essential to apply, after the application of the first electric pulse (after the last output of the first electric pulse), a square-wave electric pulse (second electric pulse: transfer pulse 1) with a low voltage for a long period of time under predetermined conditions. This is because, by virtue of the second electric pulse, the nucleic acid molecule is efficiently incorporated into the cells through the small pores (pores in the cell walls formed by the first electric pulse). It should be noted that the second electric pulse is a low-electric energy pulse having a low energy amount, and hence is free of a risk of causing damage to the cells.

It should be noted that the electrical polarity of the second electric pulse may be the same electrical polarity (the direction of the electrodes is the same) as or may be the opposite polarity (the direction of the electrodes is opposite) to that of the first electric pulse, but it is desirable that the electric pulses preferably have the same polarity.

In the second electric pulse, it is necessary to apply a voltage under a condition of 150 V/cm or less (30 V or less in the case of a 2-mm gap cuvette). It is desirable to apply a voltage of preferably 125 V/cm or less, more preferably 100 V/cm or less. The case where the voltage is excessively high is not suitable because damage to the cell walls increases, resulting in a decrease in viability.

It should be noted that the second electric pulse may be applied without any particular limitation on the lower limit of its voltage value as long as a condition for the electric energy per pulse to be described later is satisfied.

It is essential that the 'electric energy per pulse' of the second electric pulse fall within a predetermined range. It is essential that the electric energy be 0.02 J/100 μL or more. When the electric energy is excessively low, sufficient gene transfer efficiency cannot be attained. The lower limit of the electric energy may be, for example, preferably 0.04 J/100 μL or more, more preferably 0.06 J/100 μL or more, still more preferably 0.08 J/100 μL or more, particularly preferably 0.09 J/100 μL or more, even more preferably 0.1 J/100 μL or more.

In addition, it is essential that the upper limit of the total electric energy be 0.6 J/100 μL or less. The case where the electric energy is excessively high is not preferred because damage to the cell walls increases, resulting in a decrease in viability. The upper limit of the electric energy may be, for example, preferably 0.5 J/100 μL or less, more preferably 0.45 J/100 μL or less, still more preferably 0.4 J/100 μL or less, particularly preferably 0.35 J/100 μL or less, even more preferably 0.3 J/100 μL or less, still even more preferably 0.25 J/100 μL or less.

In consideration of the foregoing in a comprehensive manner, it is suitable that the electric energy per pulse be 0.02 to 0.6 J/100 μL, preferably 0.04 to 0.5 J/100 μL, more preferably 0.06 to 0.4 J/100 μL, still more preferably 0.08 to 0.3 J/100 μL, particularly preferably 0.09 to 0.25 J/100 μL, even more preferably 0.1 to 0.25 J/100 μL.

In the technology of the present invention, it is required that the second electric pulse be applied two or more times. It is suitable that the number of the times be preferably 3 or more, more preferably 4 or more, still more preferably 5 or more, particularly preferably 6 or more, even more preferably 7 or more, still even more preferably 8 or more, yet still even more preferably 9 or more, particularly even more preferably 10 or more. Increasing the number of the times of the second electric pulse allows the incorporation of the nucleic acid molecule through the small pores to be performed many times, and hence transfer efficiency can be improved. The upper limit of the number of the times, which is not particularly limited, may be, for example, 20 or less. This is because, even when the number of the times is increased any further, the efficiency is not expected to be improved greatly.

It should be noted that an interval between pulses in the case of the plurality of times of the application of the pulse may be, for example, 200 msec or less, preferably 100 msec or less, more preferably 75 msec or less, still more preferably 50 msec or less.

In addition, in the present invention, the pulse length and decay rate of the second electric pulse are factors for determining the electric energy, but do not show direct correlations with gene transfer efficiency and transformation efficiency.

Third Electric Pulse: Transfer Pulse 2 (Tp2)

The electroporation treatment of the present invention is the technology for which it is essential to apply, after the application of the second electric pulse (after the last output of the second electric pulse), a square-wave electric pulse (third electric pulse: transfer pulse 2) that is opposite in electrical polarity (the direction of the electrodes is opposite) to the second electric pulse, with a low voltage for a long period of time under predetermined conditions.

By virtue of the third electric pulse, even after the completion of the incorporation of the nucleic acid molecule into the cells with the second electric pulse, the nucleic acid molecule can be further incorporated. That is, transfer efficiency can be significantly improved. It should be noted that the third electric pulse, as with the second electric pulse, is also a low-electric energy pulse having a low energy amount, and hence is an electric pulse free of a risk of causing damage to the cells.

The third electric pulse is, except for being opposite in electrical polarity, an electric pulse applied under the same conditions as the second electric pulse. That is, as various electric conditions for the third electric pulse, the same conditions as the conditions described above for the second electric pulse may be adopted.

(Culture)

The technology of the present invention is an electroporation treatment technology for 'eukaryotic algal cells with cell-wall,' and does not require treatment for converting the target algae into protoplasts. Accordingly, when the cells after the performance of the electroporation treatment through the application of the predetermined electric pulses are cultured in a general manner with a selection medium or the like, transgenic algal cells (transformed algal cells) can be obtained extremely simply.

EXAMPLES

Hereinafter, the present invention is described by way of Examples. However, the scope of the present invention is not limited to Examples shown below.

Example 1

"Electroporation Based on Square-Wave Three-Step Method"

A study was made of whether or not transformation of green algal cells still having cell walls based on an electroporation method using a cuvette electrode was able to be performed through the use of the square-wave three-step method.

(1) "Preparation of Algal Cell Solution"

First, a study was made using, as a target, *Chlamydomonas reinhardtii*, a unicellular green alga easy to analyze for transformation.

300-mL conical flasks were previously subjected to dry-heat sterilization treatment, 100 mL each of a Tris-Acetate-Phosphate medium (TAP medium) were dispensed in the flasks, and 5 mL of a liquid culture medium of *Chlamydomonas reinhardtii* (*Chlamydomonas reinhardtii* strain C-9: strain NIES-2235 from National Institute for Environmental Studies) that had been precultured on a TAP medium were inoculated therein. While being agitated at 25° C. and 100 rpm under light illumination at 50 µmol/m$^2$/sec, culture was performed until the cell concentration reached 1 to 2×10$^6$/mL (OD at 730 nm reached 0.3 to 0.4).

The algal liquid culture medium was centrifuged (at 600×g for 5 minutes), and suspended in a TS buffer (TAP medium containing 40 mM sucrose) to prepare a cell solution.

(2) "Preparation of DNA Solution"

For a region of plasmid pHyg3 (see Berthold P. et al., Protist., 153(4), p 401-412, (2002)) containing a hygromycin resistance gene aph7, a PCR reaction was performed with primers having base sequences set forth in SEQ ID NOS: 1 and 2 (with an enzyme: PrimeSTAR GXL DNA Polymerase, TAKARA, Japan) to afford a 1,999-bp DNA fragment. The fragment was purified with a PCR purification kit (QIAGEN, USA) to prepare a DNA solution.

(3) "Electric Pulse Treatment"

In a 2-mL Eppendorf tube, the cell solution and the DNA solution were thoroughly mixed at normal temperature without foaming to prepare a suspension having a final cell concentration of 1×10$^8$ cells/mL and a final DNA concentration of 10 µg/mL. 40 µL of the suspension (4×10$^6$ cells/40 µL, 400 ng/40 µL) were charged into a 2-mm gap cuvette (EC-002S NEPA cuvette electrode having a capacity of 40 to 400 µL, Nepa Gene Co., Ltd.).

The cuvette was mounted to a cuvette electrode chamber (CU500, Nepa Gene Co., Ltd.) of an electric pulse-generating device (NEPA21 (trademark), Nepa Gene Co., Ltd.) capable of generating square-wave electric pulses, and electric pulse treatment was performed based on the electroporation method involving using multiple pulses by the three steps of sequentially applying three kinds of square-wave electric pulses, i.e., the poring pulse (Pp), the transfer pulse 1 (Tp1), and the transfer pulse 2 (Tp2) (see FIG. 1) (Test Group 1-1). It should be noted that the series of operations was performed under a room temperature condition in order to prevent a water droplet from adhering to the cuvette. It should be noted that the "+" sign and the "−" sign in the table indicate the polarities of the transfer pulses, and the "+" sign shows that an electric pulse of the same polarity as the poring pulse was applied, while the "−" sign shows that an electric pulse opposite in polarity to the poring pulse was applied.

Meanwhile, as a control, electric pulse treatment was performed using a general decay wave electric pulse-generating device (Gene-Pulser, Bio-Rad) under standard conditions in the decay wave electric pulse method (Test Group 1-2).

(4) "Evaluation of Transformation Efficiency"

Within 1 minute after the completion of the electric treatment, the cell/DNA suspension was mixed with 10 mL of a TS buffer that had been prepared in a 14-mL polyethylene tube. The mixture was subjected to static culture at 25° C. for 24 hours under light illumination at 2 to 3 µmol/m$^2$/sec.

Figure 2:
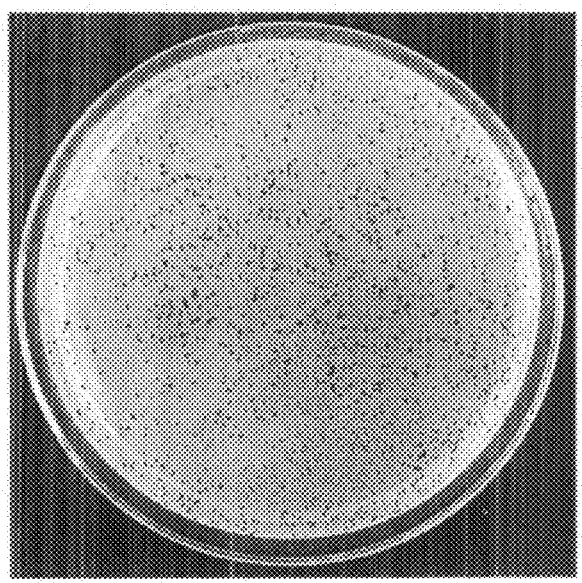
FIG. 2 is a photographic image taken of a TAP agar medium after the growth of *Chlamydomonas reinhardtii* cells transformed with a hygromycin resistance gene in Example 1, in which grown green colonies indicate colonies of *Chlamydomonas reinhardtii* having hygromycin resistance.

After the culture, the solution was centrifuged (at 600×g for 5 minutes) and the supernatant was discarded, followed by plating onto a 1.5% agar TAP medium containing 30 µg/mL hygromycin B. Static culture was performed at 25° C. under light illumination at 80 µmol/m$^2$/sec, and 4 days later, the number of hygromycin-resistant colonies was counted. Table 1 shows the results. In addition, FIG. 2 shows a photographic image of the TAP agar medium after the growth of transformed cells.

From the results, it was shown that the transformation of green algal cells (*Chlamydomonas reinhardtii*) still having cell walls was able to be performed with extremely high efficiency by performing electroporation involving sequentially applying three kinds of square-wave electric pulses, i.e, the poring pulse, the transfer pulse 1, and the transfer pulse 2 under electric conditions shown in Table 1 (Test Group 1-1).

On the other hand, when the electroporation method was performed under the standard conditions in the conventional decay wave electric pulse method, the number of green algal cells having cell walls that had been transformed was small (Test Group 1-2).

(5) "Discussion"

It was shown that the eukaryotic alga with cell-wall was transformed with extremely high efficiency by sequentially applying the three kinds of square-wave electric pulses under the above-mentioned conditions. It was shown that transfer efficiency as high as about 26 times that in the conventional method was able to be attained by the method of this example without the performance of pretreatment for the algal cells.

TABLE 1

|  |  |  | Test Group 1-1 | Test Group 1-2 |
|---|---|---|---|---|
|  | Transfer method |  | Square-wave three-step method 2-mm gap cuvette | Decay wave method 2-mm gap cuvette |
| Set values | Pp | Voltage (V) | 250 V (1,250 V/cm) | 300 V (1,500 V/cm) |
|  |  | Pulse length (ms) | 8 ms |  |
|  |  | Pulse interval (ms) | 50 ms |  |
|  |  | Number of pulses | 2 times | 1 time |
|  |  | Decay rate (%) | 40% |  |
|  |  | Pulse interval (ms) | 50 ms |  |
| Tp1, Tp2 |  | Voltage (V) | 20 V (100 V/cm), 20 V (100 V/cm) |  |
|  |  | Pulse length (ms) | 50 ms, 50 ms |  |
|  |  | Pulse interval (ms) | 50 ms, 50 ms |  |
|  |  | Number of pulses | 5 times, 5 times |  |
|  |  | Decay rate (%) | 40%, 40% |  |
|  |  | Polarity | +, − |  |
| Evaluation |  | Number of transformed cells/ μg DNA | 3,880 ± 470 | 150 ± 25 |

Example 2

"Study of Voltage Value and Pulse Length of Poring Pulse"

Regarding the electric pulse conditions of the poring pulse, a study was made of the influences of the voltage value and the pulse length on the transformation efficiency.

(1) "Electric Pulse Treatment"

In the same manner as in the method described in Example 1, a cell/DNA suspension (*Chlamydomonas reinhardtii* strain C-9: $1 \times 10^8$ cells/mL, about 2-kbp DNA fragment of pHyg3 containing aph7: 10 μg/mL) was prepared, and 40 μL of the suspension ($4 \times 10^6$ cells/40 μL, 400 ng/40 μL) were charged into a 2-mm gap cuvette.

Square-wave electric pulse treatment based on the three-step method was performed by changing, for each prepared sample, the voltage of the poring pulse to 200 V (1,000 V/cm), 250 V (1,250 V/cm), or 300 V (1,500 V/cm), and further changing the pulse length to 2 ms, 4 ms, 6 ms, or 8 ms for each voltage condition. It should be noted that 6 samples were tested for each set of conditions (a total of 72 samples). In addition, the number of times of pulses, the decay rate, and the pulse interval were set to fixed values shown in Table 2. In addition, the equipment and basic operations used in this treatment were the same as in the method described in Example 1.

(2) "Evaluation of Transformation Efficiency"

Figure 3:
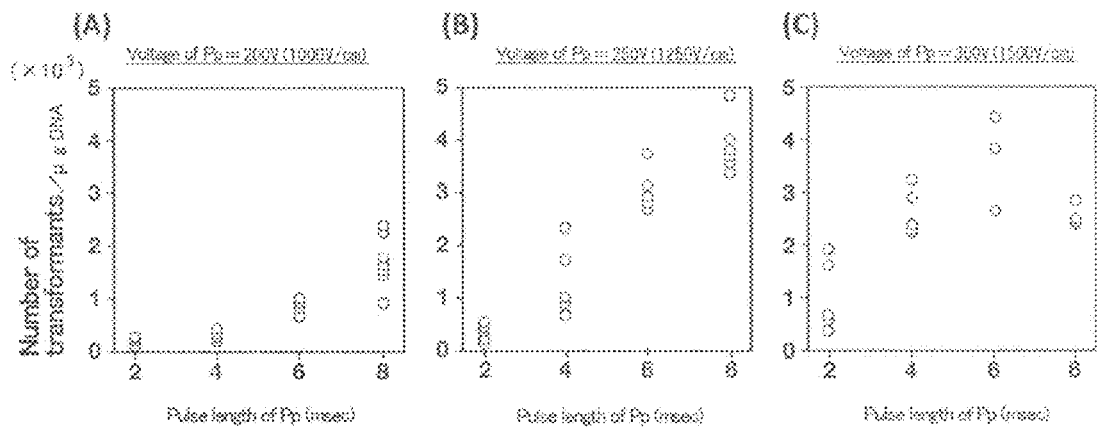
FIG. 3 are graphs showing number of transformed cells measured in Example 2, in which the vertical axis represents the number of transformed cells per μg DNA and the horizontal axis represents the pulse length (msec) of the poring pulse, FIG. 3A being a figure showing results under the condition that the voltage of the poring pulse is 200 V (1,000 V/cm), FIG. 3B being a figure showing results under the condition that the voltage of the poring pulse is 250 V (1,250 V/cm), FIG. 3C being a figure showing results under the condition that the voltage of the poring pulse is 300 V (1,500 V/cm)

In the same manner as in the method described in Example 1, the cells after the electric pulse treatment were cultured on a TAP agar medium, and the number of hygromycin-resistant colonies after the culture was counted to evaluate transformation efficiency. FIGS. 3A to 3C show the results.

From the results, it was found that, under the conditions where the voltage condition of the poring pulse was 200 V (1,000 V/cm) (FIG. 3A) or 250 V (1,250 V/cm) (FIG. 3B), when the pulse length was set to 2 to 8 ms, the number of transformants was increased as the pulse length became longer.

On the other hand, under 300 V (1,500 V/cm) (FIG. 3C), when the pulse length was set to 2 to 6 ms, the transfer efficiency was likely to be increased as the pulse length became longer and the number of transformants peaked when the pulse length was 6 ms. In addition, when the pulse length was set to 8 ms, there was observed such a tendency that the number of transformants slightly reduced.

In addition, when the case of 8 ms under the condition of 250 V (1,250 V/cm) (FIG. 3B) and the case of 8 ms under the condition of 300 V (1,500 V/cm) (FIG. 3C) were compared, there was observed such a tendency that the number of transformants was higher under the condition of the lower voltage, i.e, 250 V (1,250 V/cm).

(3) "Discussion"

From the results, it was shown that the transformation efficiency in this method had close relationships with the electric conditions of the poring pulse, but did not have simple proportional relationships with the voltage value, the current value, and the like.

TABLE 2

|  | Transfer method |  | Square-wave three-step method 2-mm gap cuvette |
|---|---|---|---|
| Set values | Pp | Voltage (V) | 200 to 300 V (1,000 to 1,500 V/cm) |
|  |  | Pulse length (ms) | 2 to 8 ms |
|  |  | Pulse interval (ms) | 50 ms |
|  |  | Number of pulses | 2 times |
|  |  | Decay rate (%) | 40% |
|  |  | Pulse interval (ms) | 50 ms |
| Tp1, Tp2 |  | Voltage (V) | 20 V (100 V/cm), 20 V (100 V/cm) |
|  |  | Pulse length (ms) | 50 ms, 50 ms |
|  |  | Pulse interval (ms) | 50 ms, 50 ms |
|  |  | Number of pulses | 5 times, 5 times |
|  |  | Decay rate (%) | 40%, 40% |
|  |  | Polarity | +, − |

Example 3

"Study of Electric Energy of Poring Pulse"

Regarding the electric pulse conditions of the poring pulse, a study was made of the influence of the electric energy on the transformation efficiency.

(1) "Electric Pulse Treatment"

In the same manner as in the method described in Example 1, a cell/DNA suspension (*Chlamydomonas reinhardtii* strain C-9: $1 \times 10^8$ cells/mL, about 2-kbp DNA fragment of pHyg3 containing aph7: 10 μg/mL) was prepared, and 40 μL of the suspension ($4 \times 10^6$ cells/40 μL, 400 ng/40 μL) were charged into a 2-mm gap cuvette.

Figure 4:
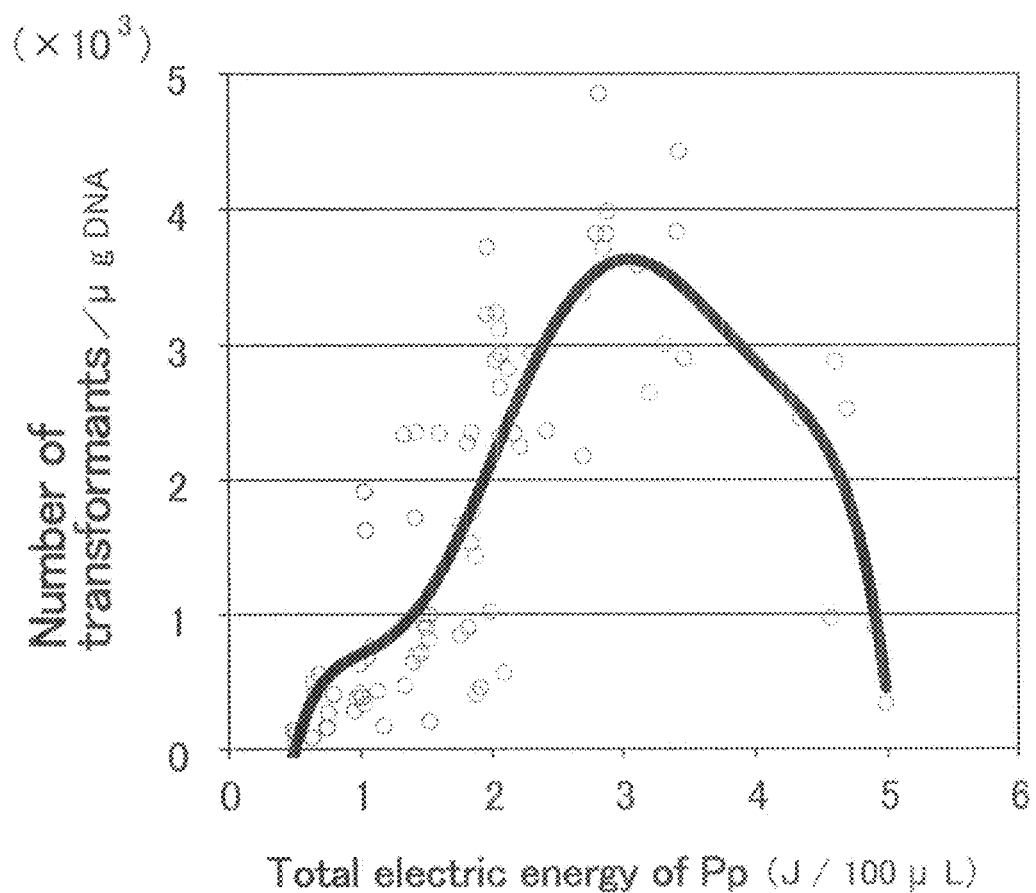
FIG. 4 is a graph showing number of transformed cells measured in Example 3, in which the vertical axis represents the number of transformed cells per μg DNA and the horizontal axis represents the total electric energy of the poring pulse (J/100 μL)

Square-wave electric pulse treatment based on the three-step method was performed for a total of 84 samples by changing, for each prepared sample, the total electric energy (J/100 μL) of the poring pulse within horizontal axis values shown in FIG. 4 (within the range of 0.5 to 5 J/100 μL). It should be noted that various electric conditions were set within the ranges of values shown in Table 3. In addition, the equipment and basic operations used in this treatment were the same as in the method described in Example 1.

It should be noted that the electric energy of the initial pulse of the transfer pulses under these electric conditions showed a value of about 0.16 to 0.25 J/100 μL.

(2) "Evaluation of Transformation Efficiency"

In the same manner as in the method described in Example 1, the cells after the electric pulse treatment were cultured on a TAP agar medium, and the number of hygromycin-resistant colonies after the culture was counted to evaluate transformation efficiency. FIG. 4 is the graph showing the results. It should be noted that, in the graph, an approximation curve was prepared from a set of points plotted for the respective data.

From the results, it was found, regarding the transformation efficiency in this method, that, when the total electric energy of the poring pulse fell within the range of 1.3 to 4.9 J/100 μl, there was such a tendency that transformed cells were obtained at about 1,000 cells/μg DNA or more, and high transfer efficiency that was about 6.7 or more times as high as the value of the related art (decay wave method: see Test Group 1-2), i.e., about 150 cells/μg DNA was provided.

In addition, it was found that, in the range of 1.7 to 4.8 J/100 μL, there was such a tendency that transformed cells were obtained at about 1,500 cells/μg DNA or more, and higher transfer efficiency that was about 10 or more times as high as that in the related art was provided.

In addition, it was found that, in the range of 1.9 to 4.6 J/100 μL, there was such a tendency that transformed cells were obtained at about 2,000 cells/μg DNA or more, and particularly high transfer efficiency that was about 13.3 or more times as high as that in the related art was provided.

In addition, it was found that, in the range of 2.1 to 4.3 J/100 μL, there was such a tendency that transformed cells were obtained at about 2,500 cells/μg DNA or more, and additionally high transfer efficiency that was about 16.7 or more times as high as that in the related art was provided.

In addition, it was found that, in the range of 2.4 to 3.8 J/100 μL, there was such a tendency that transformed cells were obtained at about 3,000 cells/μg DNA or more, and additionally high transfer efficiency that was about 20 or more times as high as that in the related art was provided.

In addition, it was found that, in the range of 2.7 to 3.3 J/100 μL, there was such a tendency that transformed cells were obtained at about 3,500 cells/μg DNA or more, and more additionally high transfer efficiency that was about 23.3 or more times as high as that in the related art was provided.

In addition, it was found that, at around 3 J/100 μL, there was such a tendency that transformed cells were obtained at about 3,700 cells/μg DNA or more, and the highest transfer efficiency that was about 24.7 times as high as that in the related art was provided.

(3) "Discussion"

From the results, it was revealed that the transformation efficiency in this method had a close relationship with the total electric energy of the poring pulse, and the above-mentioned optimum range existed.

TABLE 3

| Transfer method | | Square-wave three-step method 2-mm gap cuvette |
|---|---|---|
| Set values | Pp Voltage (V) | 200 to 300 V (1,000 to 1,500 V/cm) |
| | Pulse length (ms) | 2 to 8 ms |
| | Pulse interval (ms) | 50 ms |
| | Number of pulses | 1 to 3 times |
| | Decay rate (%) | 10 to 40% |
| | Pulse interval (ms) | 50 ms |
| Tp1, Tp2 | Voltage (V) | 20 V (100 V/cm), 20 V (100 V/cm) |
| | Pulse length (ms) | 50 ms, 50 ms |
| | Pulse interval (ms) | 50 ms, 50 ms |
| | Number of pulses | 5 times, 5 times |
| | Decay rate (%) | 40%, 40% |
| | Polarity | +, − |

Example 4

"Study of DNA Concentration"

A study was made of the influence of the DNA concentration in a solution on the transformation efficiency, in the preparation of a cell/DNA suspension.

(1) "Electric Pulse Treatment"

Cell/DNA solutions (*Chlamydomonas reinhardtii* strain C-9: $1\times10^8$ cells/mL, about 2-kbp DNA fragment of pHyg3 containing aph7: 1 to 100 μg/mL) having DNA concentrations show in Table 4 were prepared, and 40 μL of each of the solutions ($4\times10^6$ cells/40 μL, 40 ng to 4 μg/40 μL) were charged into a 2-mm gap cuvette. For each prepared sample, square-wave electric pulse treatment based on the three-step method was performed under the electric conditions shown in Test Group 1-1 of Example 1 (total electric energy of poring pulse=2.69 to 3.11 J/100 μL, electric energy of initial pulse of transfer pulses=about 0.16 to 0.25 J/100 μL). In addition, the equipment and basic operations used in this treatment were the same as in the method described in Example 1.

(2) "Evaluation of Transformation Efficiency"

Figure 5:
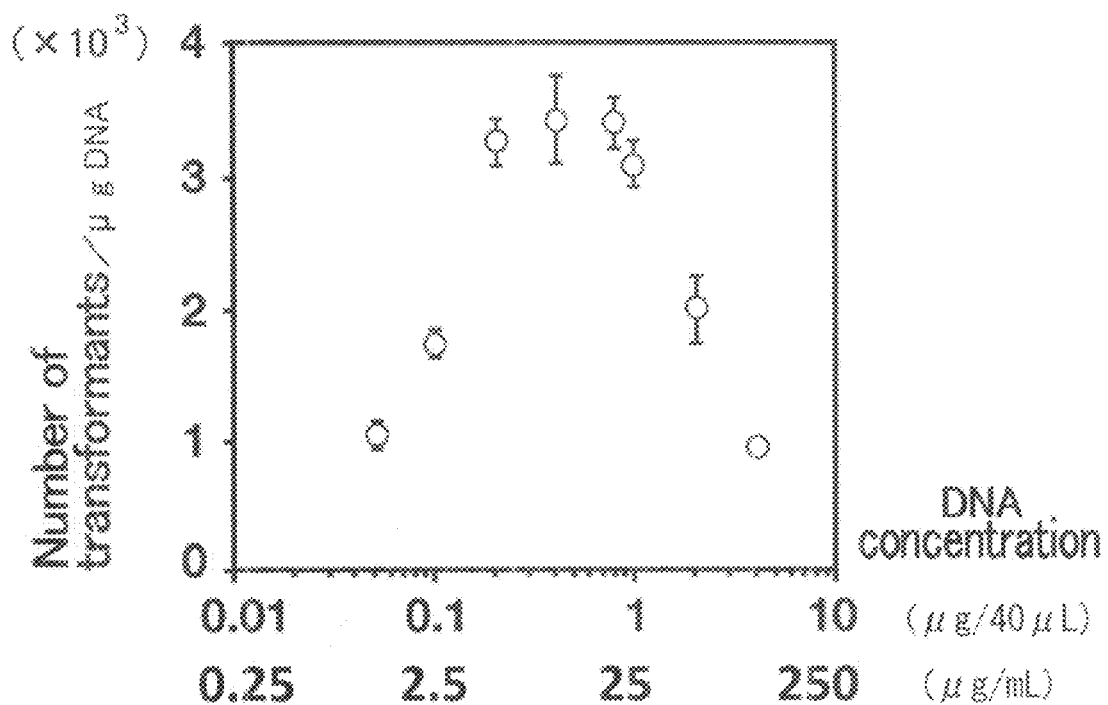
FIG. 5 is a graph showing number of transformed cells measured in Example 4, in which the vertical axis represents the number of transformed cells per μg DNA and the horizontal axis represents DNA concentration.

In the same manner as in the method described in Example 1, the cells after the electric pulse treatment were cultured on a TAP agar medium, and the number of hygromycin-resistant colonies after the culture was counted to evaluate transformation efficiency. Table 4 and FIG. 5 show the results.

From the results, it was shown that transformation with a transfer efficiency of about 1,000 cells/μg DNA or more was able to be performed through the use of this method even when any of the solutions prepared so as to have a wide range of DNA concentrations, i.e., DNA concentrations of 1.25 to 100 μg/mL was used. It was also shown that transformation with an efficiency of 1,700 cells/μg DNA or more was able to be performed with the solutions prepared to have the DNA concentration between 2.5 to 50 μg/mL.

Specifically, it was shown that the number of transformed cells sharply rose along with an increase in DNA concentration up to a DNA concentration of 5 μg/mL, and a remarkably high transfer efficiency of 3,000 cells/μg DNA or more was provided when the DNA concentration was between 5 to 25 μg/mL.

(3) "Discussion"

From the results, it was shown, regarding the transformation efficiency in this method, that transformation with high efficiency was able to be performed using solutions having a wide range of DNA concentrations, i.e., DNA concentrations of 1.25 to 100 μg/mL. In particular, it was shown that transformation with remarkably high efficiency was able to be achieved when the DNA concentration was 2.5 to 50 μg/mL, most preferably 5 to 25 μg/mL.

TABLE 4

| Test Group | DNA concentration (μg/mL) | Number of transformed cells/μg DNA |
|---|---|---|
| 4-1 | 1.25 | 1,028 ± 51 |
| 4-2 | 2.5 | 1,700 ± 4211 |
| 4-3 | 5 | 3,268 ± 140 |
| 4-4 | 10 | 3,443 ± 316 |
| 4-5 | 20 | 3,390 ± 121 |
| 4-6 | 25 | 3,080 ± 141 |
| 4-7 | 50 | 1,988 ± 258 |
| 4-8 | 100 | 953 ± 6 |

Example 5

"Test for Expression and Function of Exogenous Fluorescent Protein"

A study was made of whether or not an exogenous fluorescent protein (reporter gene product) was able to be expressed and allowed to function through the use of plasmid DNA into which an exogenous gene had been incorporated in the preparation of a cell/DNA suspension.

(1) "Preparation of DNA Solution"

Plasmid DNA (about 7,800 bp) of pTT1-LciB-GFP (see Yamano T. et al., Plant Cell Physiol., 51, p 1453-1468, (2010)) was prepared using *Escherichia coli* and a plasmid extraction kit, and a solution of DNA linearized with a restriction enzyme KpnI was prepared.

(2) "Electric Pulse Treatment"

Cell/DNA solutions (*Chlamydomonas reinhardtii* strain C-9: 1×10$^8$ cells/mL, about 7.8-kbp DNA fragment of pTT1-LciB-GFP: 10 μg/mL) using the plasmid DNA were prepared, and 40 μL of each of the solutions (4×10$^6$ cells/40 μL, 400 ng/40 μL) were charged into a 2-mm gap cuvette. For each prepared sample, square-wave electric pulse treatment based on the three-step method was performed under the electric conditions shown in Test Group 1-1 of Example 1 (total electric energy of poring pulse=2.69 to 3.11 J/100 μL, electric energy of initial pulse of transfer pulses=about 0.16 to 0.25 J/100 μL). In addition, the equipment and basic operations used in this treatment were the same as in the method described in Example 1.

(3) "Evaluation of Transformation Efficiency"

Figure 6:
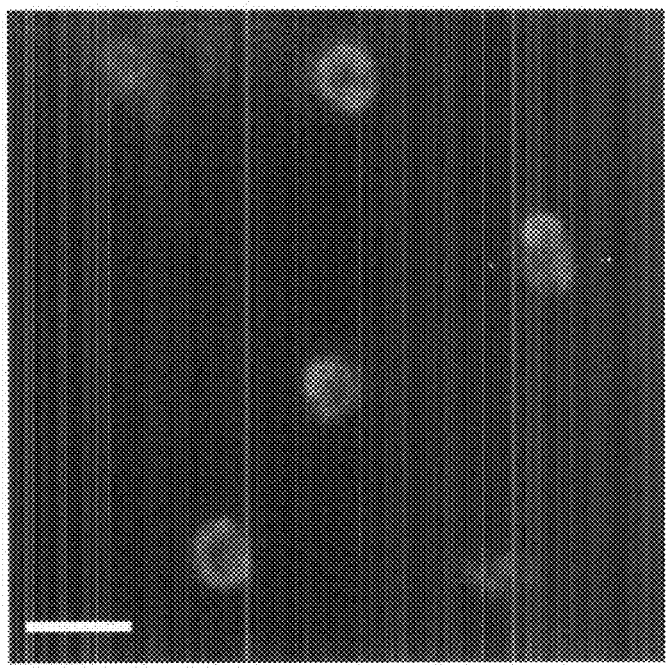
FIG. 6 is a photographic image taken of cells transformed with pTT1-LciB-GFP with a fluorescence microscope in Example 5, in which green portions indicate GFP fluorescence and in which the bar represents 5 μm.

In the same manner as in the method described in Example 1, the cells after the electric pulse treatment were cultured on a TAP agar medium, and the number of hygromycin-resistant colonies after the culture was counted to evaluate transformation efficiency. In addition, FIG. 6 shows a photographic image taken with a fluorescence microscope (BZ-9000 KEYENCE, Japan) by detecting fluorescence at 510 nm with excitation light at 490 nm.

From the result, it was shown that, even when plasmid DNA of about 7.8 kb was used, transformation with a transfer efficiency of about 500 cells/μg DNA was able to be performed. In addition, it was confirmed that GFP fluorescence-emitting transformants were generated from the transformed cells (see FIG. 6).

(4) "Discussion"

From the result, it was shown that, through the use of this method, plasmid DNA was able to be efficiently transferred to transform eukaryotic algal cells with cell-wall and the exogenous protein was able to be expressed and allowed to function normally.

It should be noted that the reason why the number of transformed cells in this example showed a lower value than the numbers of transformed cells in other examples was presumably because the DNA as the object to be transferred was longer.

Example 6

"Study of Transfer Pulse"

A study was made of the influence of the number of times of the transfer pulse on the transformation efficiency.

(1) "Electric Pulse Treatment"

In the same manner as in the method described in Example 5, cell/DNA solutions (*Chlamydomonas reinhardtii* strain C-9: 1×10$^8$ cells/mL, about 7.8-kbp DNA fragment of pTT1-LciB-GFP: 10 μg/mL) were prepared, and 40 μL of each of the solutions (4×10$^6$ cells/40 μL, 400 ng/40 μL) were charged into a 2-mm gap cuvette. For each prepared sample, square-wave electric pulse treatment based on the three-step method was performed under the electric conditions shown in Table 5-A (total electric energy of poring pulse=1.51 to 1.56 J/100 μL, electric energy of initial pulse of transfer pulses=about 0.22 to 0.23 J/100 μL). In addition, the equipment and basic operations used in this treatment were the same as in the method described in Example 1.

It should be noted that the numbers of times of the transfer pulse 1 (Tp1) and the transfer pulse 2 (Tp2) under these electric conditions were set to numbers shown in Table 5-B.

(2) "Evaluation of Transformation Efficiency"

In the same manner as in the method described in Example 1, the cells after the electric pulse treatment were cultured on a TAP agar medium, and the number of hygromycin-resistant colonies after the culture was counted to evaluate transformation efficiency. Table 5-B shows the results.

From the results, it was shown that, when the number of times of each of the transfer pulses 1 and 2 was increased from 5 to 10, the gene transfer efficiency was increased, obtaining increased number of transformed cells.

(3) "Discussion"

From the results, it was shown that, when the number of times of the transfer pulse in this method was set to about 10 for each of the transfer pulse 1 and the transfer pulse 2, the transformation efficiency significantly enhanced. This was presumably because the increased numbers of times of the transfer pulses improved the transfer efficiency of DNA, which facilitated the acquirement of surviving transformed cells.

It should be noted that the reason why the number of transformed cells in this example showed a lower value than the numbers of transformed cells in other examples was probably because the value of the total electric energy of the poring pulse was lower and the DNA as the object to be transferred was longer.

TABLE 5-A

| Transfer method | | Square-wave three-step method 2-mm gap cuvette |
|---|---|---|
| Set values | Pp Voltage (V) | 200 V (1,000 V/cm) |
| | Pulse length (ms) | 5 ms |
| | Pulse interval (ms) | 50 ms |
| | Number of pulses | 2 times |
| | Decay rate (%) | 10% |
| | Pulse interval (ms) | 50 ms |
| | Tp1, Voltage (V) | 20 V (100 V/cm), 20 V (100 V/cm) |

TABLE 5-A-continued

| Transfer method | | Square-wave three-step method 2-mm gap cuvette |
|---|---|---|
| Tp2 | Pulse length (ms) | 50 ms, 50 ms |
| | Pulse interval (ms) | 50 ms, 50 ms |
| | Number of pulses | 5 or 10 times, 5 or 10 times |
| | Decay rate (%) | 40%, 40% |
| | Polarity | +, − |

TABLE 5-B

| Test Group | Numbers of times of Tps | Number of transformed cells/μg DNA |
|---|---|---|
| 6-1 | 5 each | 197.5 |
| 6-2 | 10 each | 327.5 |

Example 7

"Application to Other Green Algal Cells"

A study was made of whether or not transformation of other green algal cells was able to be performed by performing electroporation in such a manner as to satisfy the electric energy condition of the poring pulse determined above.

(1) "Electric Pulse Treatment"

Cell solutions of *Chlamydomonas reinhardtii* strains shown in Table 6 were prepared in the same manner as in the method described in Example 1, cell/DNA suspensions (green algal cells: 1×10$^8$ cells/mL, about 2-kbp DNA fragment of pHyg3 containing aph7: 10 μg/mL) were prepared, and 40 μL of each of the suspensions (4×10$^6$ cells/40 μL, 400 ng/40 μL) were charged into a 2-mm gap cuvette. For each prepared sample, square-wave electric pulse treatment based on the three-step method was performed under the electric conditions shown in Test Group 1-1 of Example 1 (total electric energy of poring pulse=2.69 to 3.11 J/100 μL, electric energy of initial pulse of transfer pulses=about 0.16 to 0.25 J/100 μL). In addition, the equipment and basic operations used in this treatment were the same as in the method described in Example 1.

(2) "Evaluation of Transformation Efficiency"

In the same manner as in the method described in Example 1, the cells after the electric pulse treatment were cultured on a TAP agar medium, and the number of hygromycin-resistant colonies after the culture was counted to evaluate transformation efficiency. FIG. 6 shows the results.

From the results, it was shown that, when the electroporation based on the three-step method was performed in such a manner as to satisfy the electric energy condition of the poring pulse determined above, the various *Chlamydomonas reinhardtii* strains were able to be transformed with high efficiency (Test Groups 7-1 to 7-4).

(3) "Discussion"

When the strain CC-125 was used as a target, the number of transformed cells showed a low value as compared to the other strains such as the strain C-9. This was presumably because the cell wall of the strain CC-125 is thicker than the cell walls of the other strains such as the strain C-9. In consideration of the results, the method of the present invention is presumably a technology that is suitably applicable even to cells of a wide range of various green algae having different cell wall thicknesses.

TABLE 6

| Test Group | Chl. strain | Electric energy of Pp (J/100 μL) | Number of transformed cells/μg DNA |
|---|---|---|---|
| 7-1 | C-9 | 2.69 to 3.11 | 3,880 ± 470 |
| 7-2 | CC-124 | 2.69 to 3.11 | 2,930 ± 471 |
| 7-3 | CC-1690 | 2.69 to 3.11 | 3,400 ± 327 |
| 7-4 | CC-125 | 2.69 to 3.11 | 1,920 ± 110 |

Example 8

"Application to Diatom Cells"

A study was made of whether or not transformation of an alga except the green alga was able to be performed by performing electroporation in such a manner as to satisfy the electric energy condition of the poring pulse determined above.

(1) "Preparation of Algal Cell Solution"

A study was made using, as a target, a diatom in a quite different evolutionary lineage from green algae and having a hard siliceous cell wall.

0.2 mM Na$_2$SiO$_3$-containing Daigo's IMK liquid medium (Nihon Pharmaceutical Co. Ltd.) supplemented with artificial sea salts (Sigma) was dispensed in conical flasks that had been subjected to dry-heat sterilization treatment, and *Phaeodactylum tricornutum* (*Phaeodactylum tricornutum* strain UTEX 642 from the University of Texas) that had been precultured was inoculated therein. In an incubator at 20° C., culture was performed under continuous light illumination at 30 μmol/m$^2$/sec with a white fluorescent lamp.

The liquid culture medium of the alga in the exponential growth phase (OD700=0.2 to 0.4) was centrifuged (at 700×g for 4 minutes), washed with a 0.77 M mannitol aqueous solution, and then suspended in a 0.77 M mannitol aqueous solution containing 8% IMK.

(2) "Preparation of DNA Solution"

The sGFP gene (sgfp) or the GUS gene (uidA) was inserted as a reporter gene into a multiple cloning site of plasmid pPha-T1 (plasmid containing a cassette having a bleomycin resistance gene bound downstream of the fcpB promoter (see Zaslayskaia L A. et al. J. Phycol., 36, p 379-386 (2000)).

Plasmid DNA having this construct was prepared using *Escherichia coli* and a plasmid extraction kit, and a solution of DNA linearized with a restriction enzyme NdeI was prepared.

(3) "Electric Pulse Treatment"

A cell/DNA solution using the above-mentioned plasmid DNA (*Phaeodactylum tricornutum* strain UTEX 642: 2.5× 10$^7$ cells/mL, DNA fragment of pPha-T1 having inserted therein sgfp or uidA: 50 μg/mL) was prepared, and 40 μL of the solution (1×10$^6$ cells/40 μL, 2 μg/40 μL) were charged into a 2-mm gap cuvette. Square-wave electric pulse treatment based on the three-step method was performed for a total of 26 samples by changing, for each prepared sample, the total electric energy (J/100 μL) of the poring pulse within horizontal axis values shown in FIG. 7 (within the range of 0.01 to 17.6 J/100 μL). It should be noted that various electric conditions were set within the ranges of values shown in Table 7. In addition, the equipment and basic operations used in this treatment were the same as in the method described in Example 1.

It should be noted that the electric energy of the initial pulse of the transfer pulses under these electric conditions showed a value of about 0.17 to 0.39 J/100 μL.

(4) "Evaluation of Transformation Efficiency"

Within 1 minute after the completion of the electric treatment, the cell/DNA suspension was mixed with 4 mL of Daigo's IMK liquid medium that had been prepared in a 14-mL polyethylene tube. The mixture was subjected to static culture at 20° C. for 20 hours under light illumination at 30 µmol/m²/sec. It should be noted that the growth rate of *Phaeodactylum tricornutum* is slow, and hence few cells divide during the culture.

Figure 7:
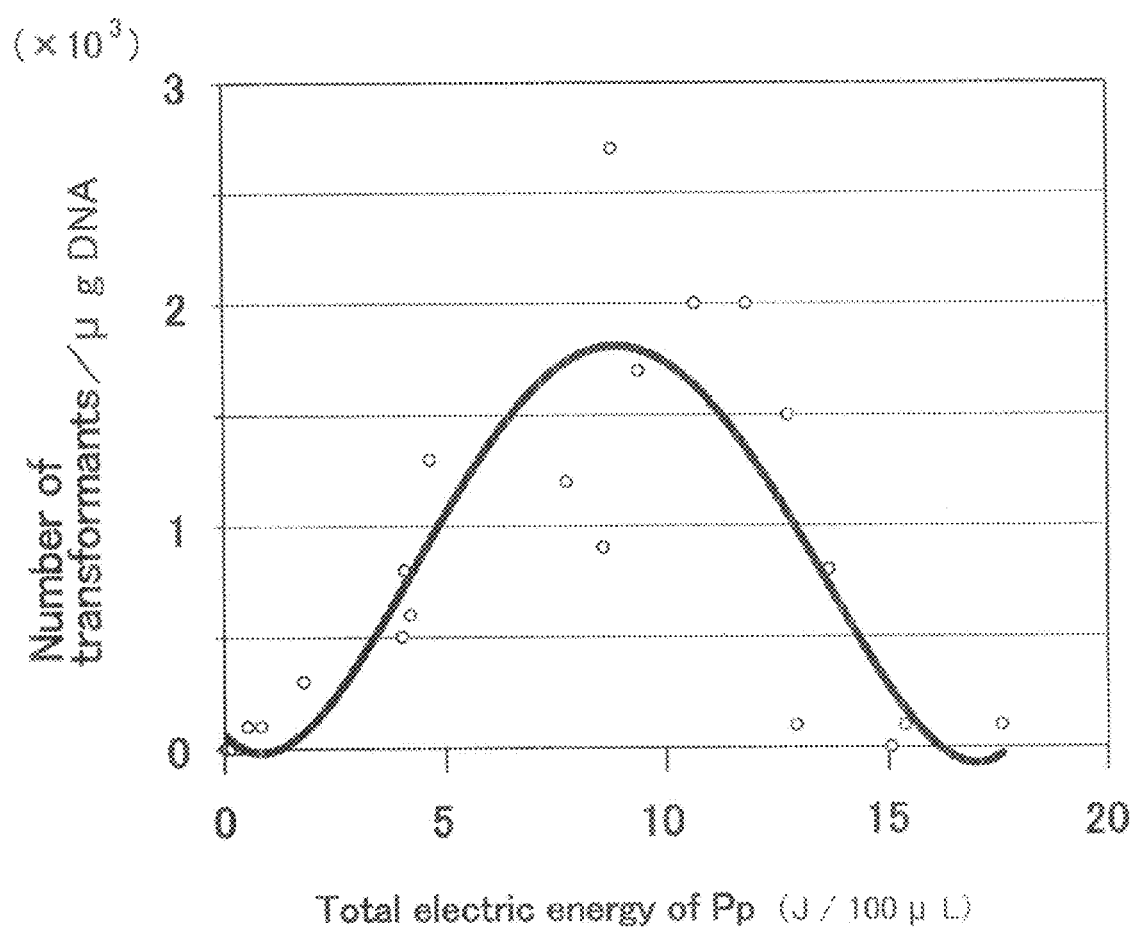
FIG. 7 is a graph showing number of transformed cells measured in Example 8, in which the vertical axis represents the number of transformed cells per μg DNA and the horizontal axis represents the total electric energy of the poring pulse (J/100 μL)

After the culture, the medium was centrifuged (at 700×g for 4 minutes) and the supernatant was discarded, followed by suspension in 0.2 mL of Daigo's IMK liquid medium. The suspension was plated onto 1% agar Daigo's IMK medium containing 100 µg/mL Zeocin™ (Invirtogen). Static culture (recovery culture) was performed at 20° C. for 20 hours under light illumination at 30 µmol/m²/sec, and 10 days later, the number of colonies having zeocin resistance was counted to evaluate transformation efficiency. FIG. 7 is a graph showing the results. It should be noted that, in the graph, an approximation curve was prepared from a set of points plotted for the respective data.

Figure 8:
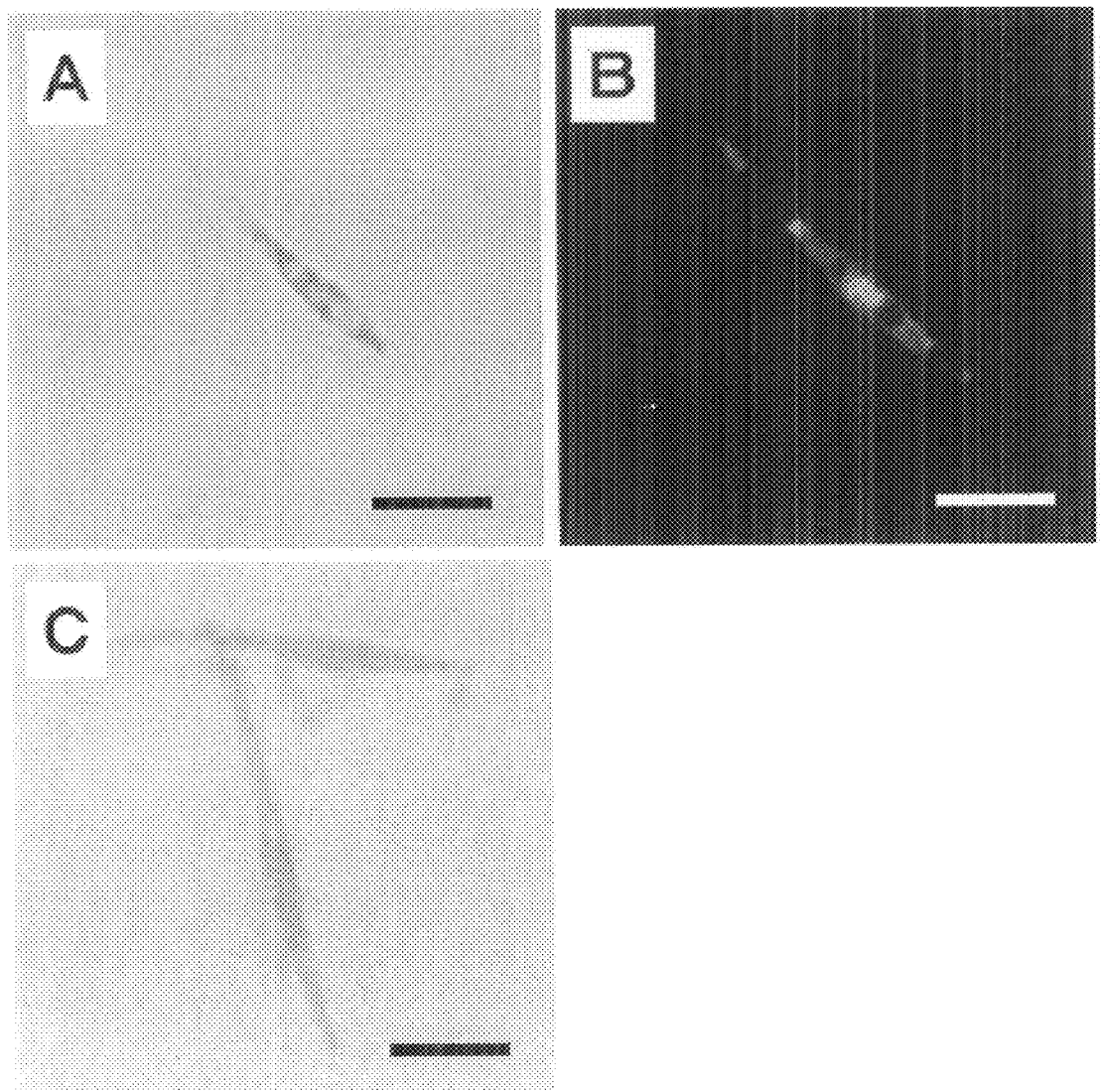
FIG. 8 are photographic images taken of cells transformed with pPha-T1-sGFP-GUS in Example 8, in which the bar represents 10 μm, FIG. 8A being a photographic image taken with a microscope under visible light, FIG. 8B being a photographic image taken with a fluorescence microscope, in which green portions indicate GFP fluorescence, FIG. 8C being a photographic image taken with a microscope under visible light after GUS staining, in which blue portions indicate portions stained with GUS.

In addition, the expression and function of the reporter gene in zeocin-resistant colonies were confirmed. FIG. 8A shows a photographic image taken of transformed cells with a microscope under visible light. In addition, FIG. 8B shows a photographic image taken with a fluorescence microscope (BZ-9000 KEYENCE, Japan) by detecting fluorescence at 510 nm with excitation light at 490 nm. In addition, FIG. 8C shows a photographic image taken with a microscope under visible light after GUS staining.

From the results, it was found that, when the total electric energy of the poring pulse fell within the range of 3.3 to 14.3 J/100 µL, there was such a tendency that transformed cells were obtained at about 500 cells/µg DNA or more, showing that high transfer efficiency was provided.

In addition, it was found that, in the range of 4.8 to 12.9 J/100 µL, there was such a tendency that transformed cells were obtained at about 1,000 cells/µg DNA or more, showing that high transfer efficiency was provided.

In addition, it was found that, in the range of 6.5 to 11.3 J/100 µL, there was such a tendency that transformed cells were obtained at about 1,500 cells/µg DNA or more, showing that high transfer efficiency was provided.

In addition, it was found that, in the range of 7.5 to 10.2 J/100 µL, there was such a tendency that transformed cells were obtained at about 1,700 cells/µg DNA or more, showing that high transfer efficiency was provided.

In addition, it was found that, at around 8.9 J/100 µL, there was such a tendency that transformed cells were obtained at about 1,850 cells/µg DNA or more, showing that high transfer efficiency was provided.

It should be noted that, when genomic DNA was extracted from the resultant zeocin-resistant colonies (transformed cells) and a PCR reaction was performed with primers specific for the sgfp gene or the uidA gene, amplified fragments of the sgfp gene or the uidA gene were detected from genomic DNA of all transformed cells.

In addition, from about 90% of the zeocin-resistant colonies, GFP fluorescence was observed and GUS staining was confirmed. That is, it was confirmed that, in most of the transformed cells, the expression and function of the exogenous protein (expression and function of the reporter gene) occurred normally.

(5) "Discussion"

From the results, it was revealed that, in order to perform gene transfer through the application of multiple square-wave pulses in three steps to the diatom, it was necessary to adjust the condition for the total electric energy of the poring pulse within the above-mentioned optimum range.

It was found that the range of the total electric energy of the poring pulse suitable for performing gene transfer into the *Phaeodactylum tricornutum* was higher than the range of the total electric energy suitable for performing gene transfer into the green alga *Chlamydomonas reinhardtii*. This was presumably because the outer layer of the diatom *Phaeodactylum tricornutum* was surrounded by a cell wall, i.e., a siliceous thick frustule.

TABLE 7

| Transfer method | | Square-wave three-step method 2-mm gap cuvette |
|---|---|---|
| Set values | Pp Voltage (V) | 50 to 300 V (250 to 1,500 V/cm) |
| | Pulse length (ms) | 1 to 90 ms |
| | Pulse interval (ms) | 50 ms |
| | Number of pulses | 1 to 9 times |
| | Decay rate (%) | 40% |
| | Pulse interval (ms) | 50 ms |
| | Tp1, Voltage (V) | 20 V (100 V/cm), 20 V (100 V/cm) |
| | Tp2 Pulse length (ms) | 50 ms, 50 ms |
| | Pulse interval (ms) | 50 ms, 50 ms |
| | Number of pulses | 5 times, 5 times |
| | Decay rate (%) | 40%, 40% |
| | Polarity | +, − |

The gene transfer and transformation technology of the present invention is expected to be a technology that promotes advances in commercial utilization of and academic research on many useful eukaryotic algae (in particular, for example, algae that produce oils and fats to be used as biofuels).

The present invention provides the electroporation technology that is directly applicable to eukaryotic algal cells with cell-wall. In addition, the technology enables gene transfer and transformation to be performed for eukaryotic algal cells with high efficiency and good reproducibility.

Thus, in the present invention, the need to prepare protoplasts prior to electric pulse treatment or to produce a cell wall-less strain is obviated, and hence the technology is an extremely highly general-purpose technology that is widely applicable to green algae and diatoms irrespective of species of algae. That is, the method of the present invention is expected to be a technology that is suitably applicable to useful green algae and diatoms for which a gene transfer method has not been established.

It should be noted that gene transfer and transformation based on the electroporation method for diatoms are important achievements attained for the first time by the present invention.

In view of the foregoing, the gene transfer and transformation technology of the present invention is expected to be a technology that promotes advances in commercial utilization of and academic research on many useful eukaryotic algae (in particular, for example, algae that produce oils and fats to be used as biofuels).

What is claimed is:

1. A method of transferring an exogenous gene into a green alga cell, the method comprising performing electroporation using multiple square-wave pulses by the following steps:
applying a square-wave electric pulse that satisfies a condition as defined in the following item (A) to a solution one time, two times or more so that the square-wave electric pulse has a total electric energy of 1.3 to 4.9 J/100 µL, the solution comprising the green alga cell with cell-wall, and a nucleic acid molecule;
applying a square-wave electric pulse that satisfies conditions as defined in the following items (B1) and (B2) to the solution at least two times; and
applying a square-wave electric pulse that satisfies conditions as defined in the following items (C1) to (C3) to the solution at least two times:
(A) a square-wave electric pulse having a voltage per pulse of 750 V/cm or more;
(B1) a square-wave electric pulse having a voltage per pulse of 150 V/cm or less;
(B2) a square-wave electric pulse having an electric energy per pulse of 0.02 to 0.6 J/100 µL;
(C1) a square-wave electric pulse opposite in polarity to the electric pulse that satisfies the conditions as defined in the items (B1) and (B2);
(C2) a square-wave electric pulse having a voltage per pulse of 150 V/cm or less; and
(C3) a square-wave electric pulse having an electric energy per pulse of 0.02 to 0.6 J/100 µL.

2. A method of transferring an exogenous gene into a diatom cell, the method comprising performing electroporation using multiple square-wave pulses by the following steps:
applying a square-wave electric pulse that satisfies a condition as defined in the following item (A) to a solution one time, two times or more so that the square-wave electric pulse has a total electric energy of 3.3 to 14.3 J/100 µL, the solution comprising the diatom cell with cell-wall, and a nucleic acid molecule;
applying a square-wave electric pulse that satisfies conditions as defined in the following items (B1) and (B2) to the solution at least two times; and
applying a square-wave electric pulse that satisfies conditions as defined in the following items (C1) to (C3) to the solution at least two times:
(A) a square-wave electric pulse having a voltage per pulse of 750 V/cm or more;
(B1) a square-wave electric pulse having a voltage per pulse of 150 V/cm or less;
(B2) a square-wave electric pulse having an electric energy per pulse of 0.02 to 0.6 J/100 µL;
(C1) a square-wave electric pulse opposite in polarity to the electric pulse that satisfies the conditions as defined in the items (B1) and (B2);
(C2) a square-wave electric pulse having a voltage per pulse of 150 V/cm or less; and
(C3) a square-wave electric pulse having an electric energy per pulse of 0.02 to 0.6 J/100 µL.

3. The method according to claim 1, wherein the green alga cell comprises a unicellular microalga.

4. The method according to claim 1, wherein the applying of the square-wave electric pulse that satisfies the condition as defined in the item (A) is performed at least two times.

5. The method according to claim 1, wherein:
the applying of the square-wave electric pulse that satisfies the conditions as defined in the items (B1) and (B2) is performed at least five times; and
the applying of the square-wave electric pulse that satisfies the conditions as defined in the items (C1) to (C3) is performed at least five times.

6. The method according to claim 1, wherein the electroporation is performed using a cuvette electrode with a gap of 2 mm or more.

7. The method according to claim 1, wherein the green alga cell is suspended in the solution.

8. The method according to claim 2, wherein the diatom cell comprises a unicellular microalga.

9. The method according to claim 2, wherein the applying of the square-wave electric pulse that satisfies the condition as defined in the item (A) is performed at least two times.

10. The method according to claim 2, wherein:
the applying of the square-wave electric pulse that satisfies the conditions as defined in the items (B1) and (B2) is performed at least five times; and the applying of the square-wave electric pulse that satisfies the conditions as defined in the items (C1) to (C3) is performed at least five times.

11. The method according to claim 2, wherein the electroporation is performed using a cuvette electrode with a gap of 2 mm or more.

12. The method according to claim 2, wherein the diatom cell is suspended in the solution.

* * * * *